United States Patent [19]

de Graaf

[11] 4,376,730

[45] Mar. 15, 1983

[54] PREPARATION OF P-AMINOAZO-BENZENE FROM ANILINE

[75] Inventor: Johannes de Graaf, Boekelo, Netherlands

[73] Assignee: Akzo N.V., Arnhem, Netherlands

[21] Appl. No.: 243,573

[22] Filed: Mar. 13, 1981

[51] Int. Cl.³ .................. C07C 107/06; C07C 115/00; C09B 27/00

[52] U.S. Cl. .................................... 260/205; 260/140; 260/208; 564/415

[58] Field of Search ........................................ 260/205

[56] References Cited

U.S. PATENT DOCUMENTS

| | | | |
|---|---|---|---|
| 1,977,266 | 10/1934 | Dahlen | 260/205 |
| 2,538,431 | 1/1951 | Shulmar | 260/205 |
| 2,714,104 | 7/1955 | Chenicek et al. | 260/205 |
| 3,793,305 | 2/1974 | Balon | 260/154 |
| 4,018,751 | 4/1977 | Trecek | 260/205 |

FOREIGN PATENT DOCUMENTS 7703353 of 0000 Netherlands .
859221 1/1961 United Kingdom .

*Primary Examiner*—Floyd D. Higel
*Attorney, Agent, or Firm*—Stevens, Davis, Miller & Mosher

[57] ABSTRACT

In the preparation of p-aminoazobenzene by diazotization of aniline with nitrous acid followed by isomerization of the intermediate diazoamino compound, the formation of undesirable by-products is suppressed by effecting the reaction in the presence of an acrylic nitrile, an acrylic acid or ester, or butadiene.

2 Claims, No Drawings

PREPARATION OF P-AMINOAZO-BENZENE FROM ANILINE

The invention relates to a process for the preparation of p-aminoazobenzene which comprises the steps of reacting an excess of aniline with an alkali metal nitrite in a hydrochloric acid medium at a temperature below 100° C., isomerizing the resulting diazoamino compound in the same medium, neutralizing the reaction mixture and separating the resulting aqueous phase from the organic phase which contains the formed p-aminoazobenzene dissolved in aniline.

A process of the type indicated above is known from the published Patent Application No. 77 03 353. To suppress the formation of byproducts, of which particularly the so-called phenyl anilines and diazo tar are very bothersome, the reaction in this known process is carried out in the presence of elementary oxygen dissolved in the reaction liquid. Although this provision has some favourable effect, it is considered less attractive in actual practice in view of explosion hazards.

It has now been found that the formation of phenyl anilines and diazo tar may at least equally well or even more effectively be suppressed by the presence of certain other additives without the risk of the formation of explosive gas mixtures.

According to the invention the present process is characterized in causing the reaction to proceed in the presence of a compound selected from the group consisting of acrylonitrile, methacrylonitrile, methacrylic acid, alkyl methacrylate with 1 to 4 carbon atoms in the alkyl radical, and butadiene in an amount of at least about 0.1% by weight, based on the aniline.

The preparation of the p-aminobenzene is effected essentially in two steps.

In the first step diazotization of aniline with nitrite takes place in a hydrochloric acid medium with formation of diphenyl triazine as diazoamino compound. By an acid catalysed reaction this compound is subsequently rearranged or isomerized to p-amino azobenzene and a little of the corresponding ortho compound.

The formation of phenyl anilines and diazo tar is believed to predominantly take place during this rearrangement and the presence of an inhibiting additive is therefore certainly required in that stage of the process. There are no objections at all, however, to having the inhibiting additive present during diazotization.

The diazotization is primarily a reaction between aniline and nitrous acid and the latter reagent is normally generated by mixing an alkali metal nitrite with hydrochloric acid. Alternative means of generating nitrous acid are of course available to the chemist, but seldom of commercial interest.

It has been found that for the present additives to be appreciably effective they should be used in an amount of at least about 0,1% by weight, based on the total amount of aniline.

The use of amounts higher than 20% by weight has hardly any further effect and is unnecessarily detrimental to the economy of the process. Preferably, the inhibiting additive is employed in an amount of about 0,5 to 10% by weight, based on the aniline.

Upon neutralization of the acid the p-aminobenzene formed in the present process is obtained as a solute in aniline, which is separated from the aqueous phase.

Depending on its further utilization the p-aminobenzene, containing a few % by weight of o-aminoazobenzene as the only important impurity, can be recovered from the aniline in a known manner or be further processed as such in solution. The quality of the aniline solution is so good that the direct processing by catalytic hydrogenation to p-phenylene diamine, an important starting material for the preparation of aromatic polyamides, proceeds satisfactorily.

The process according to the invention is illustrated but not limited by the following examples.

EXAMPLE I

In 100-ml sample bottles test reactions were carried out with different amounts of acrylonitrile. To this end there were introduced into each bottle, provided with a magnetic stirrer, 5 ml of aniline and 1,6 ml of hydrochloric acid (30%). In addition to a blank experiment different amounts of acrylonitrile were accurately measured into the sample bottles. Subsequently, after adding 1,2 ml of $NaNO_2$ solution in water (40%), the bottles were placed in ice and agitated every now and then. After a few minutes crystals (diphenyl triazene) appeared and the bottles were kept in a thermostatted bath of 35° C. for at least 4 hours, with continuous magnetic stirring.

The contents of the bottles were neutralized with 0,7–0,8 ml of 33%-sodium hydroxyde solution, after which the aniline layer was analysed by liquid- and thin-layer chromatography. Table A gives the percentages by weight of p-aminoazobenzene (pAAB), o-aminoazobenzene (oAAB), phenyl anilines (FA) and tar found in the aniline.

TABLE A

| | ml acrylonitrile added | | | | | |
|---|---|---|---|---|---|---|
| | none | 0,01 | 0,03 | 0,1 | 0,25 | 0,75 |
| pAAB | 32,0 | 30,6 | 30,3 | 30,9 | 31,3 | 26,5 |
| oAAB | 2,30 | 2,19 | 2,48 | 2,44 | 2,28 | 2,52 |
| FA | 0,48 | 0,19 | 0,06 | 0,02 | n.m. | n.m. |
| tar | 0,55 | 0,15 | 0,06 | 0,03 | 0,01 | n.m. | n.m. = not measurable

EXAMPLE II

A larger scale experiment was carried out in a 6-l reactor provided with a cooling jacket, a stirrer and a metering device. Into the reactor there were charged 4100 g of aniline, 970 g of 30%-hydrochloric acid and 20 g of acrylonitrile besides adding no acrylonitrile for making a blank determination. Use being made of a connected thermostat, the mixture was heated to 35° C., after which a solution of 830 g of $NaNO_2$ in water (40%) was added with proper stirring, over a period of 1 hour. To complete the isomerization the reaction mixture was kept at said temperature for at least 4 hours. Next, the reaction mixture was neutralized to a pH above 8, after which the brine layer was separated. Upon analysis of the aniline layer the results summarized in Table B were found.

TABLE B

| | additive | |
|---|---|---|
| | none | acrylonitrile |
| pAAB | 20,9 | 20,7 |
| oAAB | 1,48 | 1,54 |
| FA | 0,08 | 0,01 |
| tar | 0,049 | 0,01 |

EXAMPLE III

Into a 500-ml flask provided with a stirrer and a dropping funnel there were charged 100 ml of aniline and 30 ml of hydrochloric acid (30%). The temperature of the flask was set to 40° C., after which 10 ml of methyl methacrylate were added, besides adding none for a blank determination.

Next, a solution of 20 ml of NaNO$_2$ in water (40%) was added dropwise over a period of 10 minutes. The reaction mixture was kept at the above temperature for at least 4 hours and subsequently neutralized with 12 ml of sodium hydroxyde solution (33%).

The results of the analysis of the organic reaction product are summarized in Table C.

TABLE C

|      | additive |                  |
|------|----------|------------------|
|      | none     | methylmethacrylate |
| pAAB | 23,4     | 23,1             |
| oAAB | 1,97     | 1,91             |
| FA   | 0,14     | 0,005            |
| tar  | 0,11     | 0,005            |

EXAMPLE IV

The experiment of Example III was repeated with 0,5 wt.%, based on aniline, of methacrylonitrile as the additive instead of methyl methacrylate. During the 4 hours isomerization period the temperature of the flask was held at 30° C.

Analysis of the organic product layer gave the following weight percentage figures:
pAAB—23,9
oAAB—1,70
FA—<0,01
tar—0,02

EXAMPLE V

As in Example I three sample bottles were charged with aniline and hydrochloric acid and two of these bottles were further charged with 5 μl and 50 μl, respectively, of methacrylic acid.

The diazotization was made with 1,0 ml of a 40% NaNO$_2$ solution in water, the remaining procedure being as before.

The analytical data obtained are summarized in Table D.

TABLE D

|      | μl methacrylic acid added |      |       |
|------|---------------------------|------|-------|
|      | none                      | 5    | 50    |
| pAAB | 25,1                      | 24,6 | 26,3  |
| oAAB | 1,78                      | 1,73 | 1,82  |
| FA   | 0,15                      | 0,09 | <0,01 |
| tar  | 0,22                      | 0,14 | 0,07  |

EXAMPLE VI

Example I was repeated with n-butyl methacrylate as the additive. Different amounts of this additive were accurately measured into the sample bottles and the diazotization was made with 1,2 ml of a 38,5% NaNO$_2$ solution in water.

Analysis of the aniline layer gave the percentage data summarized in Table E.

TABLE E

|      | μl n-butylmethacrylate added |      |      |      |       |      |
|------|------------------------------|------|------|------|-------|------|
|      | none                         | 5    | 15   | 50   | 150   | 500  |
| pAAB | 28,5                         | 28,5 | 29,9 | 29,8 | 30,4  | 28,7 |
| oAAB | 2,36                         | 2,07 | 2,14 | 2,19 | 2,17  | 2,16 |
| FA   | 0,30                         | 0,27 | 0,12 | 0,05 | 0,015 | n.m. |
| tar  | 0,32                         | 0,19 | 0,15 | 0,05 | 0,02  | 0,02 | n.m. = not measurable

EXAMPLE VII

Example I was repeated with butadiene as the additive. To this end two sample bottles were charged with aniline and hydrochloric acid, and the content of one of these bottles was then exposed to a stream of butadiene gas at atmospheric pressure during 15 minutes.

On closing the bottle and shaking its content a total of about 2 wt.% of butadiene appeared to have been absorbed.

Subsequently, after adding 1,0 ml of a 40% NaNO$_2$ solution in water the further procedure was carried out keeping the bottle tightly closed.

The analytical data obtained are summarized in Table F.

TABLE F

|      | additive |           |
|------|----------|-----------|
|      | none     | butadiene |
| pAAB | 26,1     | 27,7      |
| oAAB | 2.02     | 1,97      |
| FA   | 0,4      | 0,05      |
| tar  | 0,24     | <0,03     |

I claim:
1. In a process for the preparation of p-aminoazobenzene which comprises the steps of reacting an excess of aniline with an alkali metal nitrite in a hydrochloric acid medium at a temperature below 100° C., isomerizing the resulting diazoamino compound in the same medium, neutralizing the reaction mixture, and separating the resulting aqueous phase from the organic phase which contains the formed p-aminoazobenzene dissolved in aniline, the improvement comprising effecting the aforesaid reaction in the presence of a compound selected from the group consisting of acrylonitrile, methacrylonitrile, methacrylic acid, alkyl methacrylate with 1 to 4 carbon atoms in the alkyl radical, and butadiene, in an amount of at least about 0.1% but not more than 20% by weight, based on the aniline.

2. A process according to claim 1, wherein the selected compound is present in an amount of about 0,5 to 10% by weight, based on the aniline.

* * * * *